United States Patent [19]

Stupp et al.

[11] Patent Number: 6,051,272
[45] Date of Patent: Apr. 18, 2000

[54] METHOD FOR SYNTHESIZING ORGANOAPATITES ON TO SURGICAL METAL ALLOYS

[75] Inventors: Samuel I. Stupp, Chicago, Ill.; Julia Hwang, Ridgewood, N.J.

[73] Assignee: The Board of Trustees of the University of Illinois, Champaign, Ill.

[21] Appl. No.: 09/247,203

[22] Filed: Feb. 9, 1999

Related U.S. Application Data

[63] Continuation-in-part of application No. 08/818,710, Mar. 14, 1997
[60] Provisional application No. 60/013,503, Mar. 15, 1996.
[51] Int. Cl.$^7$ ................ B05D 1/36; B05D 3/10; B05D 7/14
[52] U.S. Cl. ............. 427/2.26; 427/2.27; 427/327; 427/409; 427/414; 427/435
[58] Field of Search .................. 427/2.26, 2.27, 427/2.1, 2.13, 414, 409, 329, 327, 435

[56] References Cited

U.S. PATENT DOCUMENTS

| | | | |
|---|---|---|---|
| 4,082,507 | 4/1978 | Sawyer | 623/66 |
| 4,192,021 | 3/1980 | Deibig et al. | 3/1.9 |
| 4,282,287 | 8/1981 | Geise | 427/2.26 |
| 4,340,482 | 7/1982 | Sternberg | 427/245 |
| 4,489,133 | 12/1984 | Kornberg | 427/2.13 |
| 4,565,740 | 1/1986 | Golander et al. | 424/180 |
| 4,610,692 | 9/1986 | Eitenmuller et al. | 427/245 |
| 4,652,459 | 3/1987 | Engelhardt | 427/2.27 |
| 4,713,076 | 12/1987 | Draenert | 623/16 |
| 4,744,933 | 5/1988 | Rha et al. | 424/455 |
| 4,810,784 | 3/1989 | Larm | 536/20 |
| 5,007,930 | 4/1991 | Dorman et al. | 427/2.27 |
| 5,049,403 | 9/1991 | Larm et al. | 427/2 |
| 5,061,286 | 10/1991 | Lyle | 623/16 |
| 5,133,920 | 7/1992 | Dorman et al. | 623/16 |
| 5,258,034 | 11/1993 | Furlong et al. | 623/23 |
| 5,376,120 | 12/1994 | Sarver et al. | 623/16 |
| 5,470,731 | 11/1995 | Cochrum | 427/2.1 |
| 5,567,440 | 10/1996 | Hubbell et al. | 424/484 |
| 5,589,256 | 12/1996 | Hansen et al. | 427/336 |
| 5,603,338 | 2/1997 | Beaty | 427/2.27 |
| 5,605,713 | 2/1997 | Boltang | 427/2.29 |
| 5,824,651 | 10/1998 | Nanci et al. | 427/2.26 |
| 5,876,454 | 3/1999 | Nanci et al. | 427/2.26 |
| 5,939,208 | 8/1999 | Stoy | 427/2.13 |
| 5,958,504 | 9/1999 | Lee et al. | 427/2.26 |

OTHER PUBLICATIONS

Abdel–Fattah et al., "Thermal Expansion Application To Access Calcination of Bovine Hydroxyapatite", *Thermochimica Acta*, 218:465–475, (1993).
Black, Orthopaedic Biomaterials in Research and Practice, Churchill Livingstone, New York, pp. 235–283, (1988).
Charnley, "Fracture of Fermoral Prostheses in Total Hip Replacement", Clinical Orthopaedics, 111:105–120, (1975).
Lautenschlager, et al., "Physical Characteristics of Setting of Acrylic Bone Cements", *J. Biomed. Mater/Res. Symposium*, 5(Part 1):185–196, (1974).

(List continued on next page.)

*Primary Examiner*—Diana Dudash
*Attorney, Agent, or Firm*—Rockey, Milnamow & Katz, Ltd.

[57] ABSTRACT

The present invention provides a method for growing or depositing artificial bone materials called organoapatites on a metal surgical alloy. The method involves pretreating the alloy with at least one aqueous solution of a poly(amino acid). After this pretreatment step, the organoapatites can be synthesized onto the alloy. Because most surgical implants are made from metal alloys, this method can be used to make implants which contain organoapatites may promote the formation of natural bone when placed into a human patient in vivo.

15 Claims, 13 Drawing Sheets

OTHER PUBLICATIONS

Muller–Mai et al., Nanoapatite and Organoapatite Implants in Bone, Histology and Ultrastructure of the Interface, *Journal of Biuomedical Materials Research*, 29:9–18, (1995).

Raspanti et al., "Ultrastructure of Heat–Deproteinated Compact Bone", *Biomaterials*, 15(6):433–437, (1994).

Smith, T., "The Effect of Plasma–Sprayed Coatings on the Fatigue of Titanium Alloy Implants", *J. Min. Met. Mat. Soc.*, 46:54–56, (1994).

Stupp et al., "Organoapatites: Materials For Artificial Bone. I. Synthesis and Microstructure", *Journal of Biomedical Materials Research*, 26:169–183, (1992).

Stupp et al., "Organoapatites: Materials For Artificial Bone. III. Biological Testing", *Journal of Biomedical Materials Research*, 27:301–311, (1993).

Weber, et al., "A Radiological Study of Fractures of Acrylic Cement In Relation To The Stem of a Femoral Head Prosthesis", The Journal of Bone and Joint Surgery, 57–B(3):297–301, (1975).

Figure 1
Figure 1A
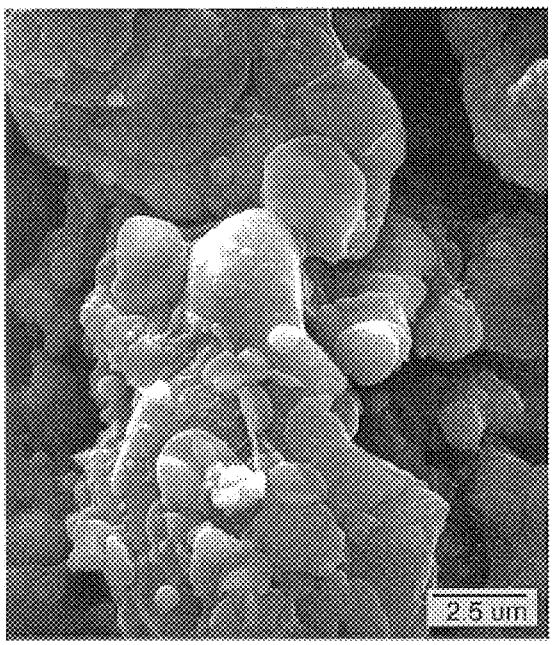
Figure 1B
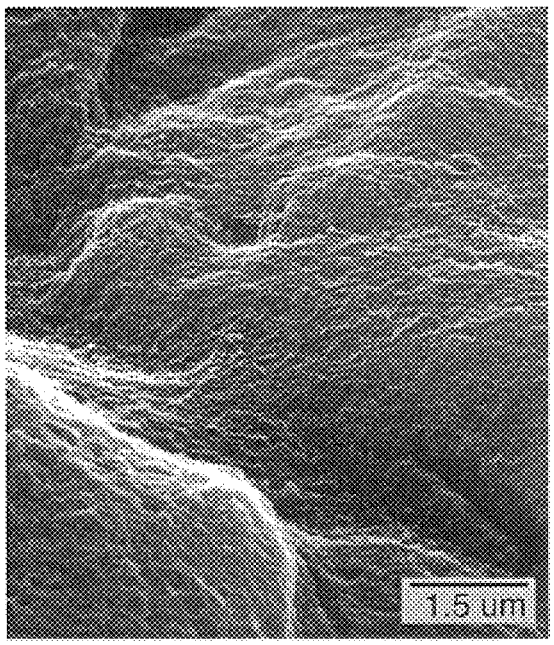
Figure 1C
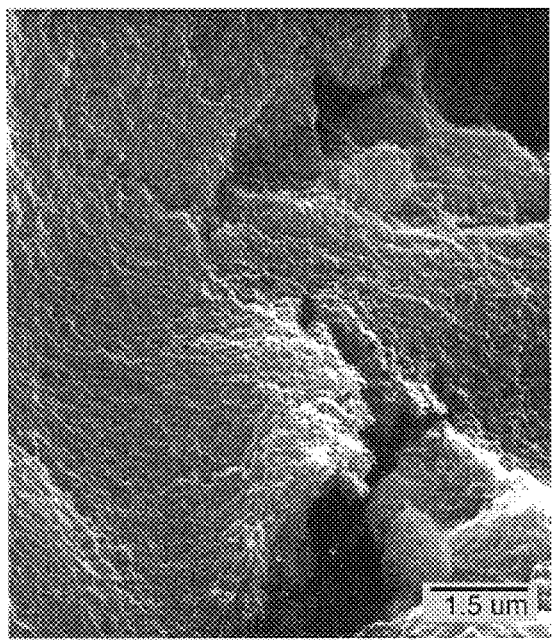
Figure 1D
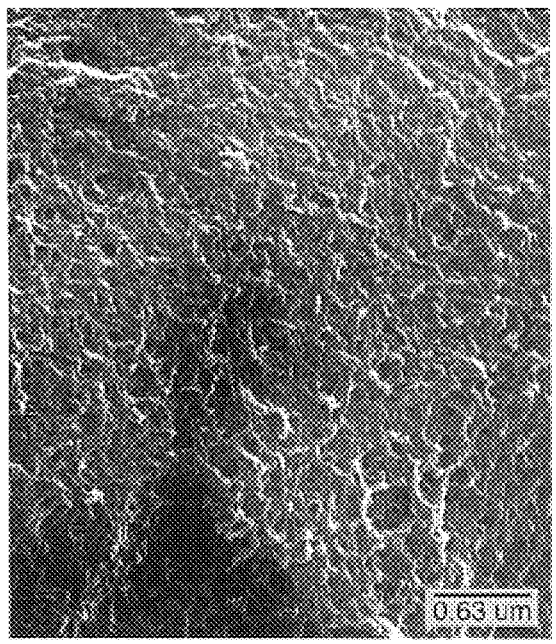

Figure 6
Figure 6A
(pLys)pLys
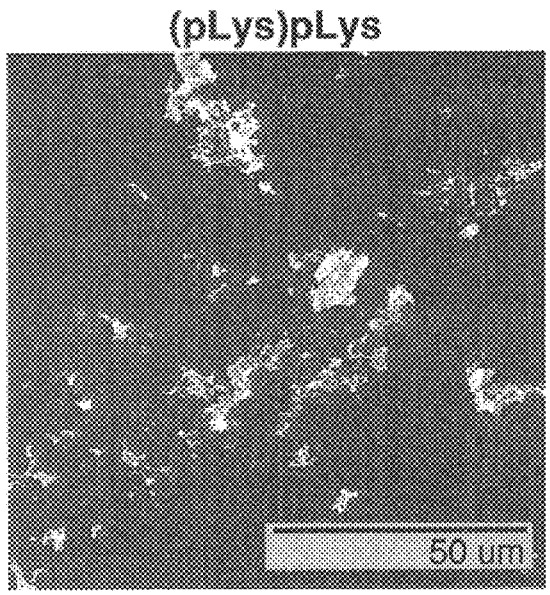
Figure 6B
(pLys,pGlu)pLys
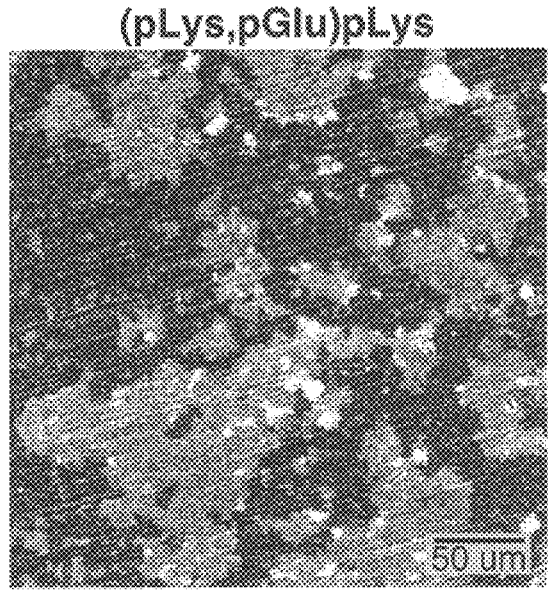
Figure 6C
(pLys)pGlu
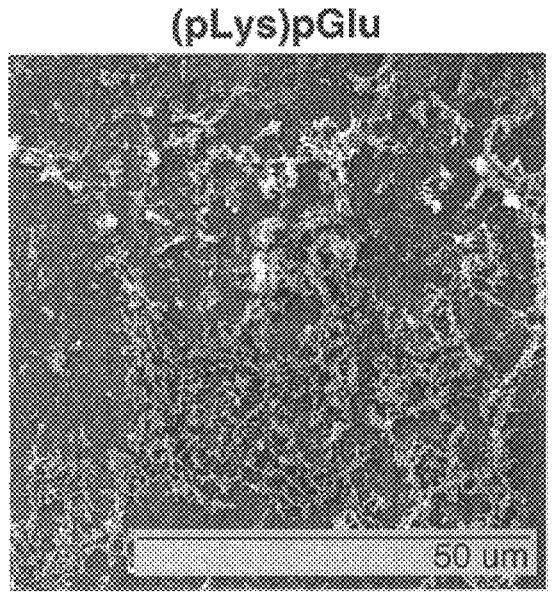
Figure 6D
(pGlu)pLys
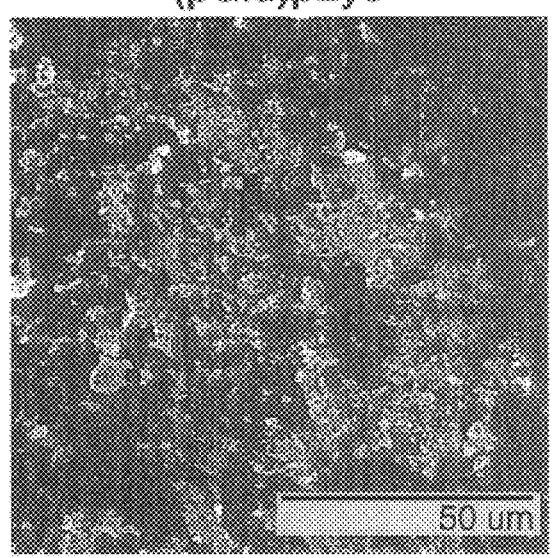

Figure 8
Figure 8A
(pLys)pLys
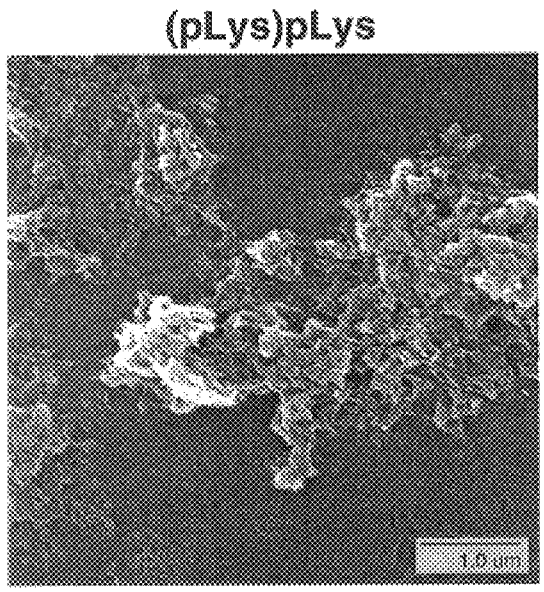
Figure 8B
(pLys,pGlu)pLys
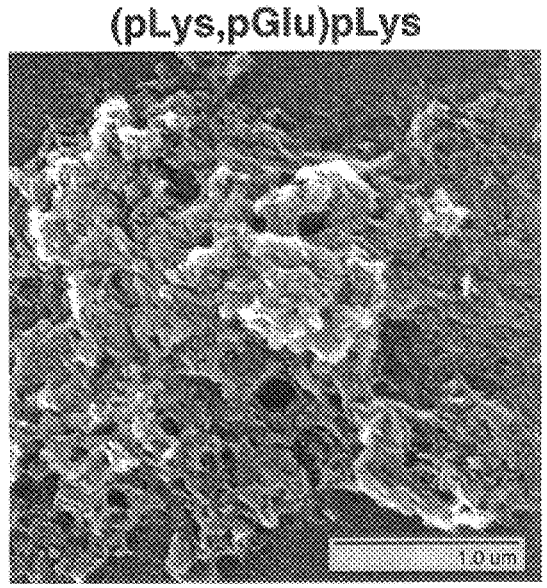
Figure 8C
(pLys)pGlu
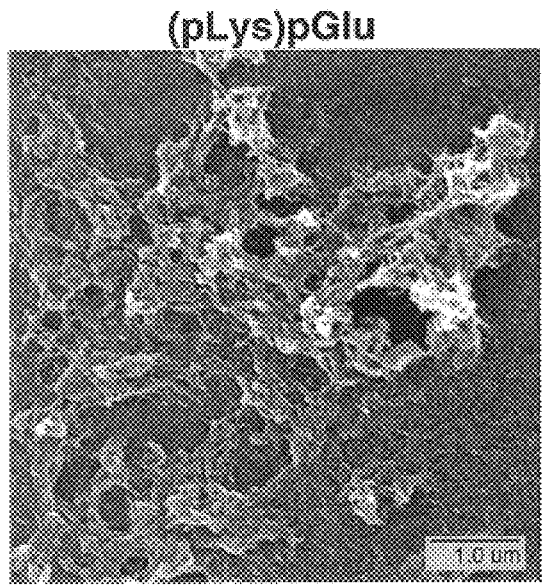
Figure 8D
(pGlu)pLys
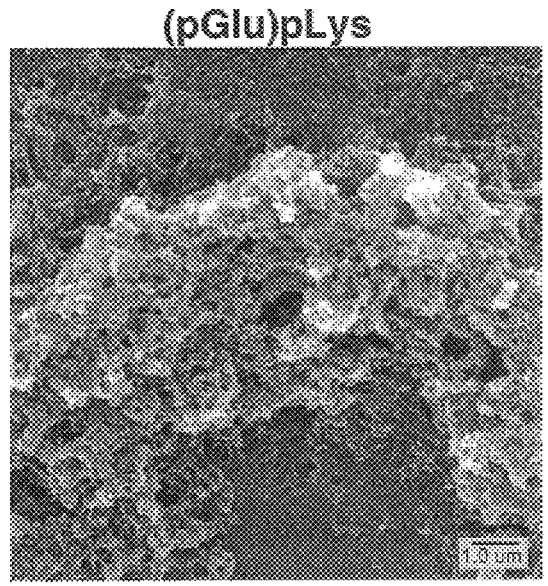

Figure 10
Figure 10A
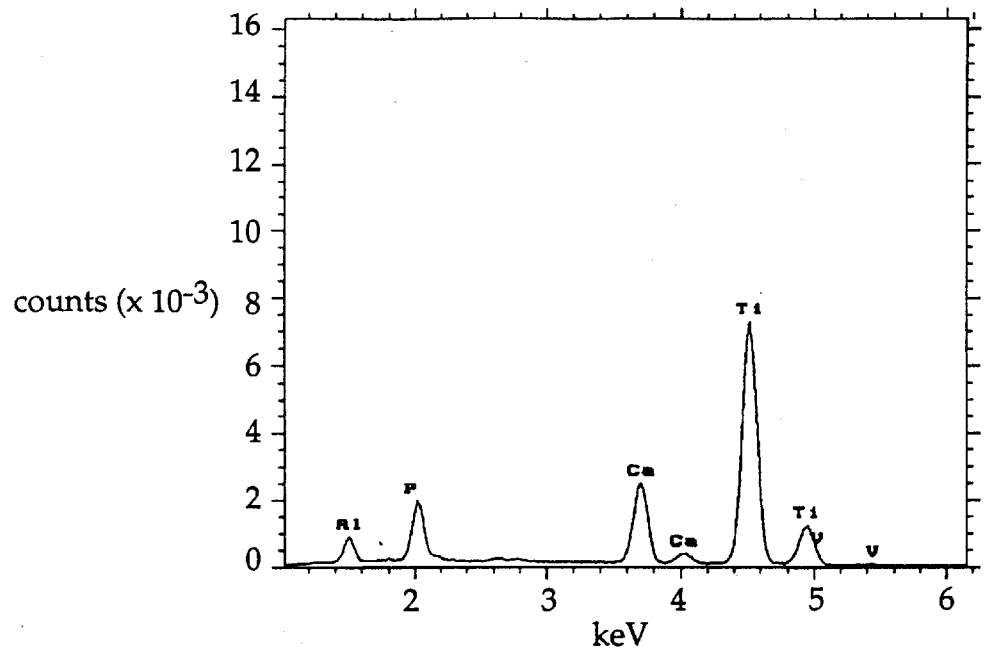
Figure 10B
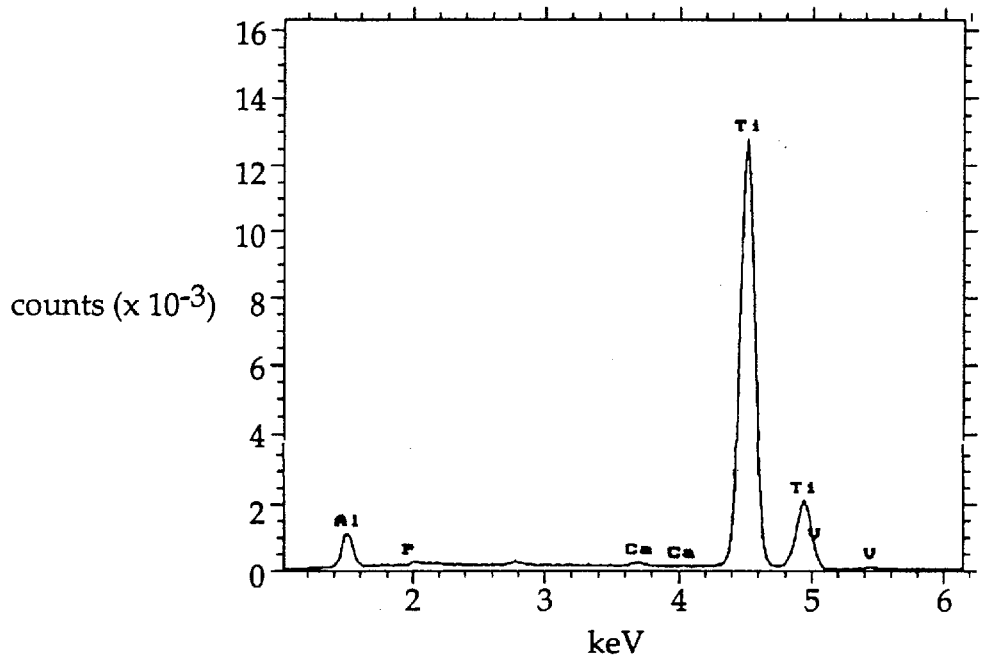

Figure 11
Figure 11A
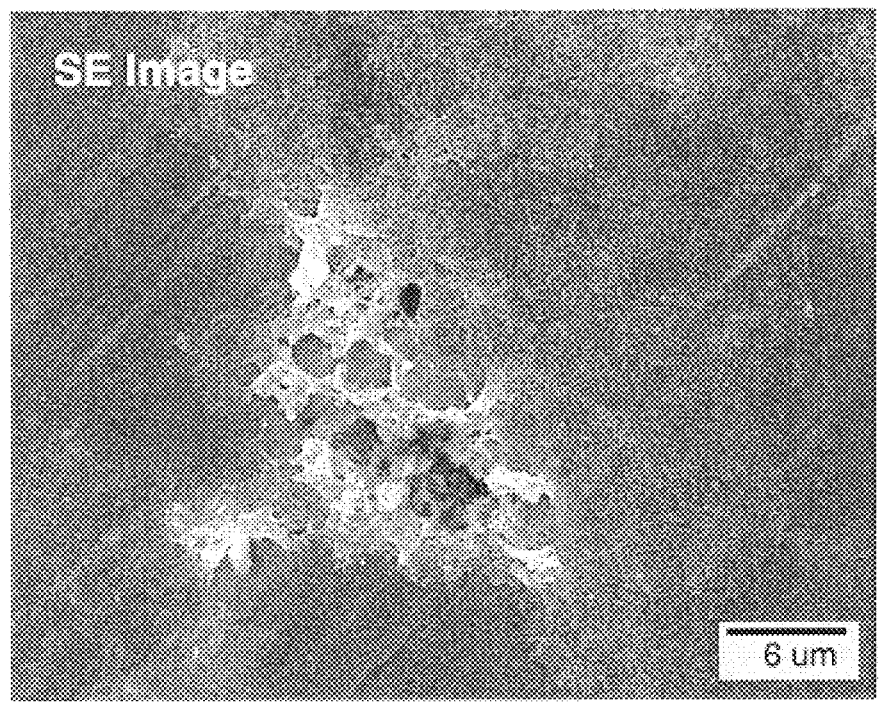
Figure 11B
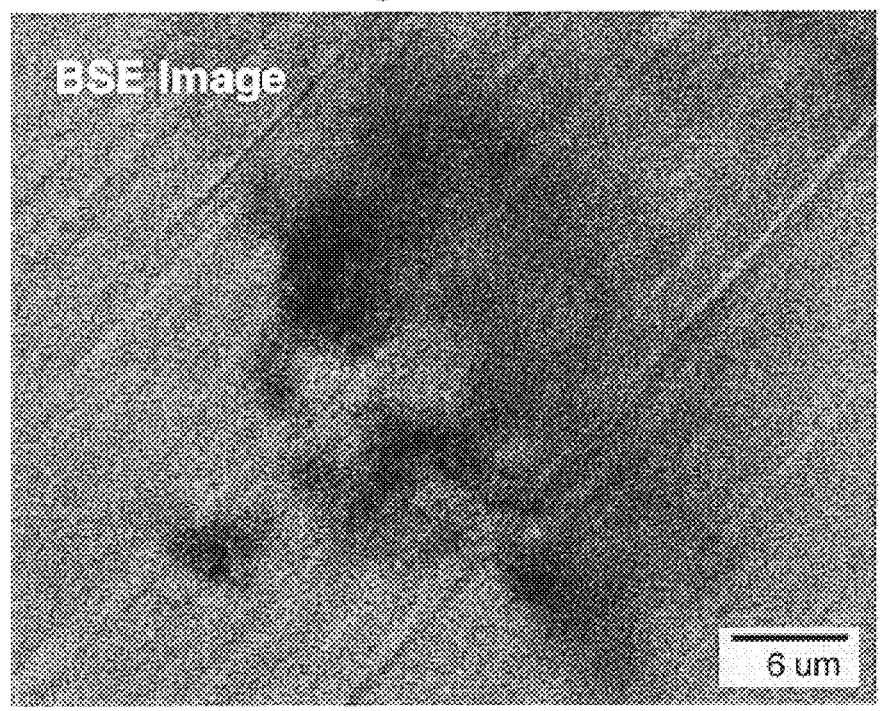

METHOD FOR SYNTHESIZING ORGANOAPATITES ON TO SURGICAL METAL ALLOYS

RELATED APPLICATIONS

This application is a continuation-in-part of U.S. Ser. No. 08/818,710 filed on Mar. 14, 1997, which claims priority from provisional application 60/013,503 filed on Mar. 15, 1996.

TECHNICAL FIELD OF THE INVENTION

The present invention relates to a method for synthesizing artificial bone materials called organoapatites on to the surface of metal alloys used in surgical procedures.

BACKGROUND OF THE INVENTION

For over thirty years, poly(methyl methacrylate) ("PMMA"), has been used as a bone cement for the fixation of orthopaedic prosthesis during joint replacement surgery. However, several problems are associated with the use of PMMA bone cement. First, thermally-induced bone necrosis has been observed adjacent to the area containing the bone cement. This necrosis has been implicated as a possible cause of prosthesis loosening. See Lautheschlager, er al., Biomed. Mater. Symp. (1974) 5:185. Second, PMMA has a low modulus and shear strength when compared to metal alloys or even natural bone. See Black, J., Orthopaedic Biomaterials in Research and Practice, Churchill Livingstone, New York (1988). While the low modulus of PMMA bone cement was initially thought to provide a "cushioning" effect by absorbing the full brunt of compressive load by elastic deformation, the modulus mismatch between the prosthesis, bone cement, and bone is believed to cause stress shielding in adjacent bone which results in a mechanically-induced resorption of tissue and eventual implant loosening. Id. Further, deterioration of the metal/cement and cement/bone interfaces, which are completely mechanical in nature and lack chemical bonding between components, are believed to cause the loosening of the prosthetic device. Id.

PMMA also exhibits poor fatigue-crack resistance and fracture toughness and frequently fractures. See, Weber, F. A., et al., J. Bone Jt. Surg. (1975), 57B: 151; Charnley, J, Clin. Orthop. Rel. Res. (1975), 111:105; Weber, F. A. et al., J. Bone J. Surg., (1975):57B 151. The fracturing of PMMA bone cement may be caused by PMMA's low tensile and shear strength, by the porosity of the cement or non-uniform thickness of the cement or by the residual tensile stresses that are induced by shrinkage of the cement upon curing. See, Ahmed, A. M., et al., Biomed. Mater. Res. Symp. Trans. (1977) 1:56. When a prosthetic device loosens, because of bone resorption, interfacial degradation or cement fragmentation, it begins to move. The movement of the prosthetic device causes pain for the patient. The only way to relieve this pain is to replace the prosthetic device.

A myriad assortment of synthetic bone substitutes and artificial bone biomaterials are known. Many of these materials are employed in place of traditional bone grafts in those instances where missing or surgically-removed bone tissue must be replaced. For example, synthetic bone is used in the resection of bone tumors, replacement of bone fragmented due to trauma, bone non-union, or in the repair of congenital defects. Typically, bone substitutes fall into two categories: nonresorbable materials, which are meant to permanently replace defects and fully or partially resorbable materials, which are intended to provide an osteoinductive template for new bone regeneration.

Xenologous bone tissue can be calcined at temperatures in excess of several hundred degrees centigrade to remove proteinaceous components which contribute to immune rejection in conventional bone grafts (Abdelfattah, W. I., et al., Thermoch. Acta, (1993), 218:465; Rapanti, M. et al., Biomaterials, (1994) 15:433). This reconstituted bone, which is usually from bovine sources, may be used in the form of a powder as an osteoinductive template for hard-tissue augmentation in a manner similar to conventional bone grafts. High temperature calcining generally results in the transformation of the original microstructure into dense, tightly packed crystals of hydroxyapatite. However, treatment at temperatures below 500° C. have been found to preserve the mineral architecture of the starting bone material while removing all of the organic components. See, Rapanti, M., et al., Biomaterials (1994) 15:433.

Current efforts have been directed to improving the rate of bone osseointegration in cementless systems by applying highly crystalline calcium phosphate coatings to the surface of porpous metal implants. The phosphate coatings are believed to invite bone growth but also consist of a brittle ceramic phase that cannot be fully resorbed. In addition, it is believed that the high processing temperatures needed to apply these coatings results in the degradation of the mechanical properties of the metal substrate. See, Smith, T., J. Min. Met. Mat. Soc., (1994) 46:54.

Alternative methods being employed involve the insertion of allografts or reconstituted bone at the metal/bone interface in an effort to invite bone regeneration. However, these methods exhibit many of the same problems associated with traditional bone graft procedures. Synthetic bone substitutes such as synthetically prepared calcium phosphates, resorbable polymer templates and conventional ceramic/polymer compositions, may not be sufficiently akin to natural tissue in the microstructure and/or composition to effectively improve growth rates.

Therefore, there is a need in the art to develop a method for growing fully or at least partially resorbable synthetic bone on the surface of a porous orthopaedic implant that can be used to stimulate cellular activity and bone growth that will eventually be replaced at least in part by natural bone tissue during osseointegration thereby eliminating the presence of a lingering mechanically brittle pure ceramic phase.

SUMMARY OF THE INVENTION

The present invention provides a method for synthesizing artificial bone materials called organoapatites on to the surface of a surgical metal alloy. The method involves treating the surface of the alloy with at least one aqueous solution of a poly(amino acid). In one aspect, the surgical alloy is immersed into a first aqueous solution containing a first poly(amino acid). The poly(amino acid) contains a functional group that has a charge. The poly(amino acid) used can be any poly(amino acid) that can be adsorbed by the metal alloy. The metal alloy is immersed in the first aqueous solution for a sufficient time for the poly(amino acid) to be adsorbed by the surface of the metal alloy.

After sufficient time in the poly(amino acid) solution, the alloy is removed for organoapafite synthesis. The treated alloy is immersed in second aqueous solution containing a second poly(amino acid) for organoapatite synthesis. The second poly(amino acid) has a functional group having a charge. The charge of the finctional group of the second poly(amino acid) is opposite to the charge of the functional group of the first poly(amino acid).

Organoapatites are synthesized on the alloy in the second aqueous solution. Once the organoapatites have been deposited on the surface of the alloy, the alloy is removed from the poly(amino acid) solution.

In another aspect, the surgical alloy is treated prior to organoapatite synthesis with two poly(amino acid) solutions. More specifically, the alloy is immersed in a first aqueous solution containing a first poly(amino acid) having a functional group having a charge. After sufficient immersion in the first poly(amino acid) solution, the alloy is removed from the solution and immersed in a second aqueous solution containing a second poly(amino acid) having a functional group having a charge that is opposite to the charge of the functional group of the first poly(amino acid). After sufficient immersion in the second poly(amino acid) solution, the alloy is removed for organoapatite synthesis. After removal, the treated alloy is immersed in a third aqueous solution containing a third poly(amino acid) for organoapatite synthesis. The third poly(amino acid) has a functional group having a charge. The charge of the functional group of the third poly(amino acid) is opposite to the charge of the second poly(amino acid). Organoapatites are then synthesized on the alloy.

BRIEF DESCRIPTION OF THE DRAWINGS

FIG. 1 shows four scanning electron micrographs (SEM) of metal plugs. FIG. 1A shows the surface of a porous surgical metal alloy plug. FIGS. 1B, 1C and 1D show the surface of the same alloy covered with organoapatite artificial bone material.

FIGS. 6A, 6B, 6C and 6D show low magnification SEM of organoapatites grown on Ti-6A1-4V surfaces. Preadsorption sequences are indicated in the parentheses.

FIGS. 8A, 8B, 8C and 8D shows high magnification SEM organoapatites grown on Ti-6Al-4V surfaces. The preadsoprtion sequence is indicated in the parentheses.

FIG. 10 shows the results of EDAX analysis. FIG. 10B shows the results of EDAX analysis of bare Ti-6Al4V alloy surfaces and FIG. 10A shows EDAX analysis of an organoapatite deposit on Ti-6Al4V surface.

FIG. 11 shows two scanning electron micrographs. FIG. 11A is a SEM of organoapatite deposits in secondary modes. FIG. 11B is a SEM of organoapatite deposits in a backscattered mode.

DETAILED DESCRIPTION OF THE INVENTION

Figure 2:
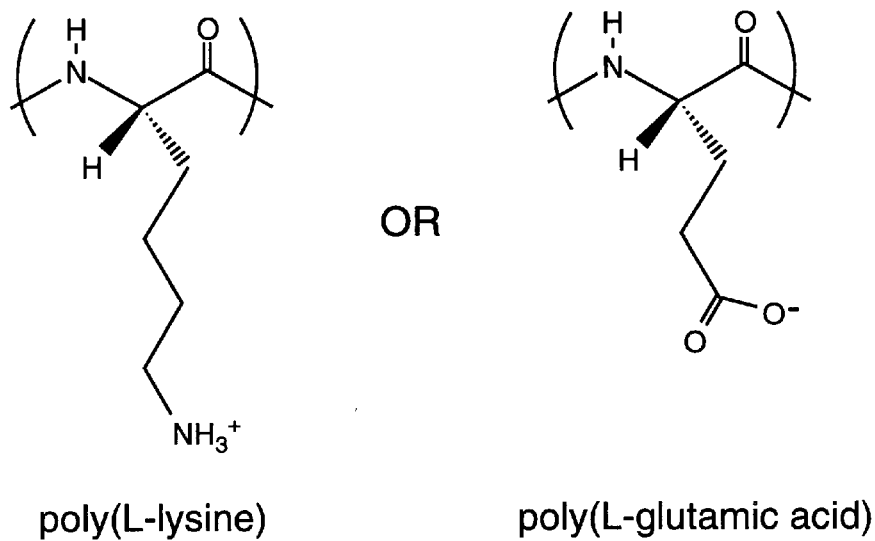
FIG. 2 shows the homogeneous liquid-phase synthesis of organoapatites.

The present invention involves a method for growing or depositing organoapatites on the surface of a surgical metal alloy. The term, "organoapatites" as used herein, refers to an artificial bone material comprising apatite crystals that contain organic material dispersed in their mineral network. Organoapatites are synthesized by nucleation and growth of apatite crystals in the presence of dissolved polypeptides or synthetic organic polyelectrolytes under certain temperature, pH an atmospheric conditions. Organoapatites contain large surface area morphologies with small crystallites which mature slowly based on the analysis of Ca/P ratios. The synthesis of organoapatites is well known in the art and is described in Stupp, S. I.; Ciegler, G. W. *J Biomed. Res.*, 1992, 26, 169, herein incorporated by reference. In this article, the authors state that it is likely that organoapatites can be prepared to contain intimate dispersions of small amounts of biomolecules such as growth factors, antibiotics, or bioadhesives. Id.

Testing of organoapatites for use as artificial bone has been reported in Stupp, S. I.; Hanson, J. A.; Eurell, J. A.; Ciegler, G. W., Johnson, A. *J. Biomed. Res.*, 1993, 27, 301 and in Muller-mai, C. M.; Stupp, S. I.; Voight, C.; Gross, U. *J Biomed. Res.* 1995, 29, 9. These articles report that organoapatites containing organic polymers such as poly (amino acid) showed excellent apposition with mineralized bone and that fibrous encapsulation was only observed when a synthetic poly(electrolyte) was the organic component. Given the biological reaction observed with organoapatites, it is believed that they should be suitable for bone replacement and that organoapatites can be used for additional functions such as the release of drugs and optimized release of antibiotics, growth factors and other substances. Id.

Cobalt-chromium, stainless steel and titanium alloys are the most common metals used in orthopaedic implants. The surface chemistry of titanium alloys in particular has been examined quite extensively as a model system in the literature with regard to its effect on tissue response in vivo.

In order for organoapatites to grow and bond to a surgical alloy, a poly(amino acid) must be adsorbed on the surface of the alloy. This is accomplished be pretreating the surface of the alloy with at least one aqueous solution of a poly(amino acid). This pretreatment step is critical, because without pretreatment, the organoapatites will not grow on the surface of the alloy. The poly(amino acids) that can be used for the pretreatment are those that can be adsorbed by the metal alloy and are soluble in an aqueous solution of high ionic strength, such as water. For example, the poly(amino acid) poly(L-lysine hydrochloride), poly(L-sodium glutamate), poly(L-sodium aspartate) and poly(glutamine) can be used in this invention. The preferred poly(amino acids) are poly (L-lysine hydrochloride) and poly(L-sodium glutamate).

The metal alloy is immersed in the poly(amino acid) solution for a sufficient amount of time to allow the poly (amino acid) to be adsorbed by the surface of the alloy. For example, the alloy can remain immersed in the poly(amino acid) solution for several minutes up to several days. Preferably, the alloy remains immersed in the poly(amino acid) solution for at least 12 hours. Most preferably, the alloy remains immersed in the poly(amino acid) solution for at least twenty (20) hours.

More than one poly(amino acid) solution can be employed in the pretreatment step. When more than one poly(amino acid) solution is employed, the alloy is immersed in the first poly(amino acid) solution for a sufficient amount of time and then removed and immersed in a second poly(amino acid) solution. Preferably, the pretreatment step utilizes two oppositely charged poly(amino acid) solutions (meaning that the poly(amino acid) in the solutions each have oppositely charged functional groups). When two oppositely charged poly(amino acids) solutions are used to pretreat the metal alloy, a poly(ionic) complex is believed to form on the surface of the alloy. It is believed that this poly(ionic) complex can be used to induce adhesion between the alloy and the organoapatites.

The aqueous solution of the poly(amino acid) may be formed be adding a poly(amino acid) such as poly(L-lysine hydrochloride) to deionized water. The pH of the poly (amino acid) solution should be maintained between about 6 to about 8, preferably about 7.4. A suitable acid (such as hydrochloride acid) or base (such as sodium hydroxide) may be added to maintain the requisite pH. Additionally, the poly(amino acid) solutions used in the present invention may be bubbled with an inert gas such as nitrogen or argon for at least five (5) hours prior to being contacted with the metal alloy in order to prevent the accumulation of carbonates on the surface of the alloy. Finally, the amount of poly(amino acid) solution used in the pretreatment step should be a least 1 mM.

Prior to pretreatment, the alloy may be cleaned by any procedure known in the art, such as ultrasonic agitation. Prior to cleaning, the alloy may be rinsed with deionized water and/or acetone. Acids such as hydrofluoric acid and nitric acid can be employed to clean the surface of the alloy. For example, a cleaning solution containing about 89 mL deionized water, about 10 mL of nitric acid and 1 mL of hydrofluoric acid can be used to clean the alloy. Regardless of whether or not the alloy is cleaned, it should be rinsed with distilled water and/or acetone prior to pretreatment.

After cleaning, the alloy is immersed in the aqueous solution of poly(amino acid) for a sufficient period of time to allow adsorption of the poly(amino acid) on the surface of the metal alloy. If the alloy is to be treated with a second poly(amino acid), the alloy is then transferred to a solution containing a second poly(amino acid) and immersed for a sufficient period of time to allow the adsorption of the second poly(amino acid). Preferably, the alloy should remain immersed in the solution containing the second poly(amino acid) for at least twelve (12) hours, and most preferably at least twenty (20) hours. The surface of the alloy may be rinsed with deionized water prior immersion in the second solution. After the metal alloy is pretreated with at least one aqueous solution of a poly(amino acid), organoapatites can be synthesized on the surface of the alloy.

Synthesis of organoapatites requires the presence of an organic polymer such as a poly(amino acid) or poly (electrolyte) as described in Stupp, S. I.; Ciegler, G. W. *J. Biomed. Res.*, 1992, 26, 169. Therefore, after pretreatment in at least one poly(amino acid) solution, the alloy may either remain in the poly(amino acid) solution in which it was pretreated or it may be removed and placed in at least 1 mM of the same or different poly(amino acid) solution or poly (electrolyte) solution. It is preferred that the alloy be removed from the poly(amino acid) solution used in the pretreatment step. It is further preferred that the alloy be placed in a poly(amino acid) solution having functional groups with a charge opposite from that of the functional groups of the poly(amino acid) solution used for the pretreatment of the alloy. If the alloy is pretreated with more than one poly(amino acid) solutions, it is preferred that alloy be placed into a poly(amino acid) solution containing functional groups having a charge opposite from the charge of the functional groups of the last poly(amino acid) solution in which the alloy was immersed during the pretreatment. While not wishing to be bound by any theory, the inventors believe that when the poly(amino acid) solution used in the pretreatment of the alloy contains functional groups having a charge opposite from the charge of the functional groups of the poly(amino acid) solution used for organoapatite synthesis, insoluble poly(ionic) complexes are formed and that these poly(ionic) complexes play an role in determining whether stable deposition of the organoapitites is obtained.

The poly(electrolyte) discussed above with respect to the pretreatment step can be used to synthesize organoapatites. The poly(electrolyte) can be any synthetic organic poly (electrolyte), such as poly(sodium acrylate), provided that it is not toxic to humans. The pH of the poly(amino acid) or poly(electrolyte) solution must be maintained between about 6 to about 8, preferably about 7.4.

As discussed earlier, the methodology for preparing organoapatites is described in Stupp, S. I.; Ciegler, G. W. *J. Biomed. Res.*, 1992, 26, 169. The first step in the synthesis of organoapatites is the preparation of solutions of $Ca(OH)_2$ and $H_3PO_4$. These solutions are prepared be adding $Ca(OH)_2$ and $H_3PO_4$ to distilled water so that the Ca/P atomic ratio equals approximately 1.67 when both are added to precipitate organoapatites. These solutions are maintained at least at room temperature, but preferably, at about 37° C. The $Ca(OH)_2$ and $H_3PO_4$ solutions are then added at an equal rate to the aqueous solution of the poly(amino acid) containing the pretreated alloy. This mixture is now referred to as the "reaction or mother liquor". The pH of the reaction or mother liquor is monitored and adjusted as needed by the addition of a base or acid to maintain a pH at about 7.4. The alloy remains in the reaction or mother liquor for a sufficient amount of time to allow for the formation of organoapatites. More specifically, the alloy may remain in the reaction liquor for at least a few minutes and up to a one day.

After the alloy has been in the reaction liquor for a sufficient amount of time to allow the organoapatites to deposit, the alloy is removed from the reaction or mother liquor, rinsed in a reagent-grade acetone and deionized $H_2O$ and dried under vacuum. If necessary, the alloy may be centrifuged to remove the bulk organoapatite by product.

The method of this invention may be used to coat the surface of surgical metal alloy with organoapatites. Since most orthopaedic implants are constructed from metal alloys, the implant can be coated with organoapatites and placed into a patient. The coating of organoapatites on the implant's surface can be partially biodegradable and natural formation induced in the patient.

By way of example and not limitation, the following examples are provided.

EXAMPLE 1

Synthesis of Organoapatites $Ca(OH)_2$ solutions were prepared by addition of 0.5557 g $Ca(OH)_2(s)$ (Sigma, St. Louis, Mo.) to 500 mL of deionized $H_2O$. $H_3PO_4$ solutions were prepared by addition of 0.4400 g $H_3PO_4(l)$ (Mallinckrodt, Paris, Ky.) to 500 ml of deionized $H_2O$. Each of these solutions were contained in separate 1000 mL triple-neck round-bottom flasks and sealed by rubber septa, and the flasks were suspended in a heated water bath maintained at about 37° C.

Figure 3:
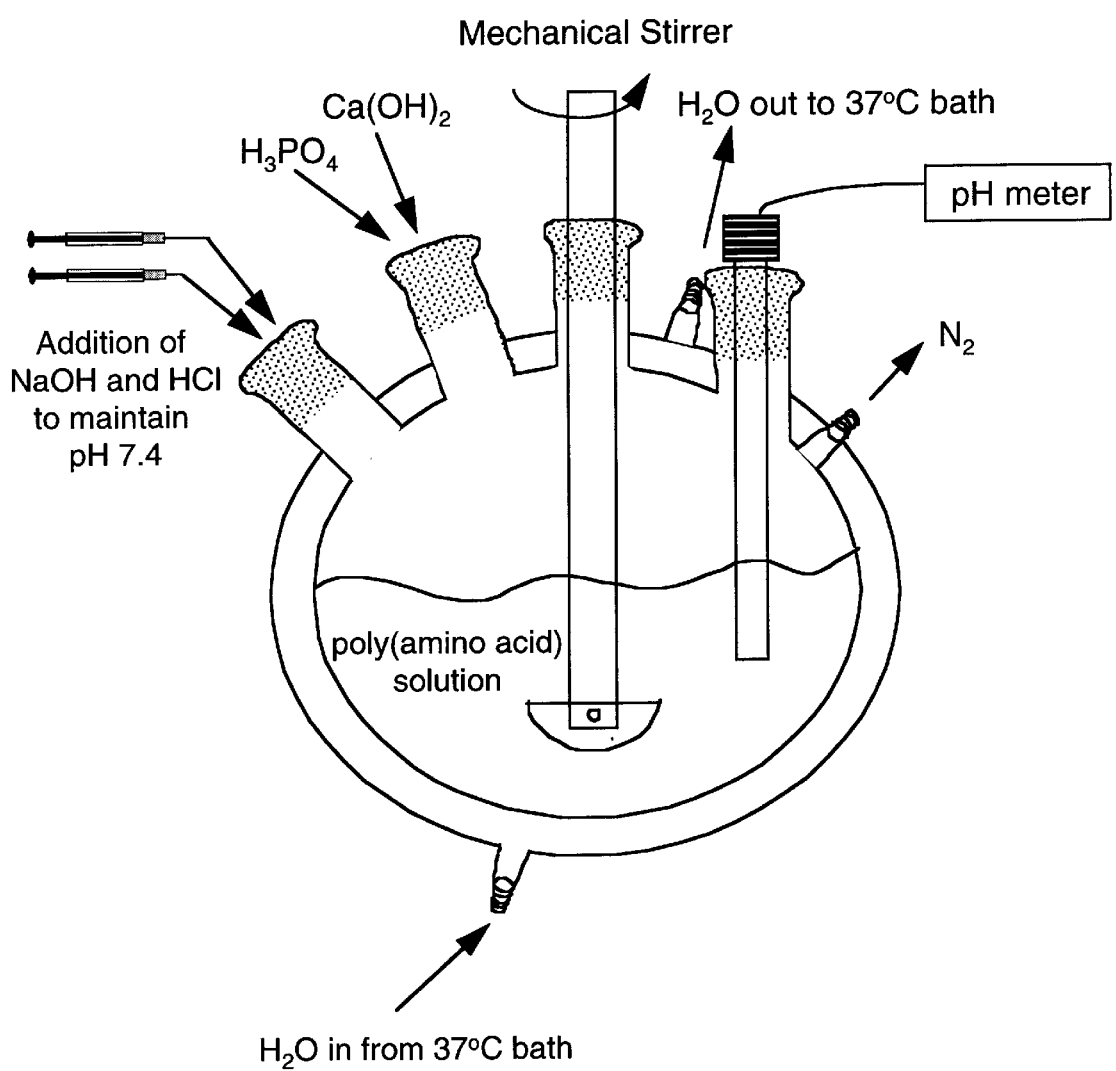
FIG. 3 is an example of an apparatus that can be used for homogeneous liquid-phase synthesis of organoapatites.

1 mM poly(amino acid) solutions were prepared by the addition of 0.0666 g poly(L-lysine hydrochloride), (Sigma, St. Louis, Mich.) or 0.0628 g poly(L-sodium glutamate) (Sigma, St. Louis, Mich.) to 400 mL deionized $H_2O$ contained in a 2 L double-walled glass reactor vessel. An example of such a device is provided in FIG. 3. For the control hydroxyapatite synthesis, the poly(amino acid) solution was replaced by 400 mL deionized $H_2O$. In all cases, water from the constant temperature bath was continuously pumped through the outer jacket of the reactor vessel to maintain a temperature of 37° C. The appropriate poly (amino acid) solution or $H_2O$ control was mechanically stirred at 125 rpm, and pH was measured by a pH-meter (Omega, Stamford Conn.) coupled to a hard-copy printer and manually adjusted to a pH of about 7.4 prior to the transfer of reactants by the dropwise addition of 6M NaOH or HCl. A glass, refillable Ag/AgCl electrode with an extended 120 mnm body was used for insertion into 24/40 flask necks. $N_2(g)$ was bubbled through all solutions to purge dispersed $CO_2$ and thus prevent incorporation of carbonate in the final product.

$Ca(OH)_2$ and $H_3PO_4$ solutions were transferred to the double-walled reactor vessel through stainless-steel cannulae at equal rates by pressurization with $N_2(g)$. Transfer was accomplished as quickly as practicable; complete transfer was accomplished in approximately 5 minutes. The pH of the reaction liquor was monitored simultaneously to reactant transfer and pH was adjusted manually as needed by the dropwise addition of NaOH and HCl to maintain a pH of about 7.4. After 1 hour, the mother liquor was centrifuged at 12,500 rpm in UHMW-polyethylene tubes and the supernatant decanted. The remaining precipitates were washed in reagent-grade acetone (Baxter, Muskegon, Mich.) and deionized $H_2O$ before drying for 24 hours by vacuum desiccation. The dried powder was ground by mortar and pestle, weighed, and stored in sealed glass vials at 5° C.

Organoapatite and control hydroxyapatite products were evaluated by X-ray diffraction to confirm formation of hydroxyapatites. Samples of product were also submitted for wet chemical analysis (Department of Chemistry, University of Illinois at Urbana/Champaign) to evaluate calcium, phosphorous and organic content. Results were in accord with expectations.

EXAMPLE 2

Growth of Organoapatites on a Surgical Alloy Surface—Metal Foils 1 mM solutions of poly(L-lysine hydrochloride) (Sigma, St. Louis, Mich.) and poly(L-sodium glutamate) (Sigma, St. Louis, Mich., were prepared as described in Example 1 in 1000 mL three-neck round bottom flasks. Poly(amino acid) solutions were adjusted to a pH of about 7.4 by the dropwise addition of 6M NaOH or HCl and sealed. The sealed solutions were then purged by bubbling nitrogen.

Ti-6Al-4V foils (Goodfellow, Cambridge UK), 0.043 mm thick and in the as received annealed condition, were cut into 5 mm×5 mm specimens and prepared according to ASTM F86. The specimens were subjected to ultrasonic agitation (for cleaning purposes) consecutively in reagent-grade acetone and deionized $H_2O$ for 15 minutes each, followed by passivation in 40% (by volume) nitric acid (Mallinckrodt) for 30 minutes. Specimens were then rinsed thoroughly in deionized $H_2O$.

Figure 4:
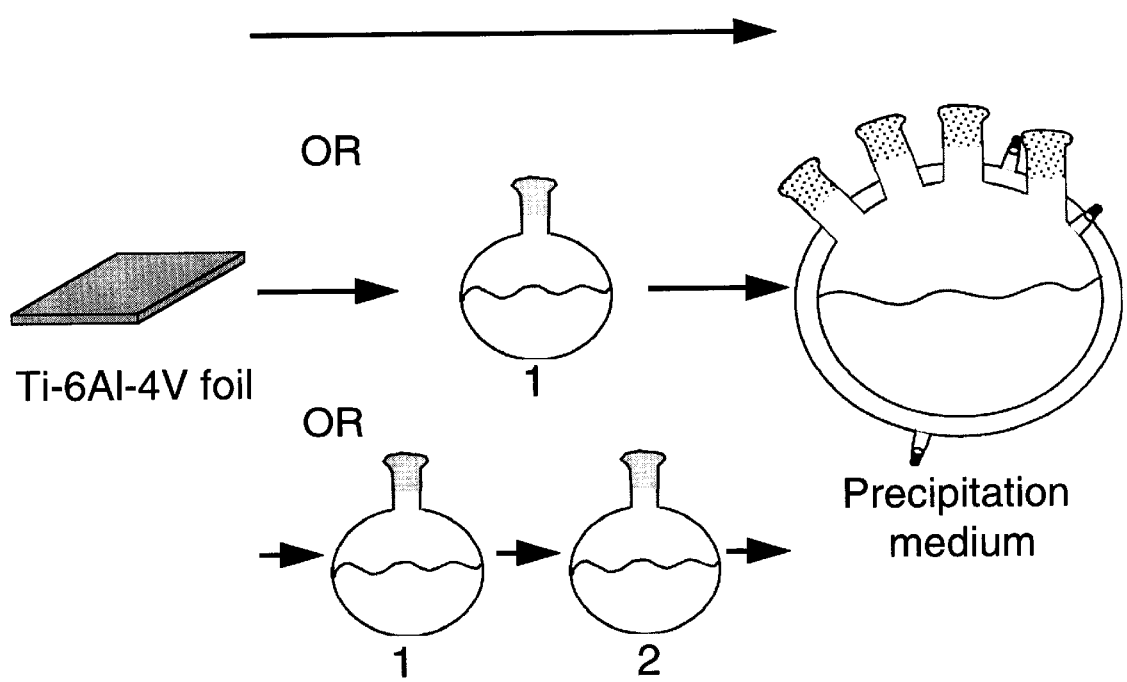
FIG. 4 shows an overall scheme to examine growth of organoapatites on a surgical alloy surface. In one case, the foil is directly immersed in the precipitation medium, in the other two, the foil is exposed to either one or two pretreatments.

Foil specimens were mounted on a custom-designed poly(tetrafluoroethylene) stage before immersion in specific sequences of poly(amino acid) solutions or direct transfer to the appropriate apatite growth medium. A summary of experimental variables studied is provided in Table 1 below and the overall scheme for growing of organoapatites on the foils is depicted in FIG. 4.

TABLE 1

| Poly(amino acid) adsorption 1 12 hours, pH 7.4, 25° C. | Poly(amino acid) adsorption 2 12 hours, pH 7.4, 25° C. | Precipitation medium 1 hour, pH 7.4, 37° C. $Ca(OH)_2$, $H_3PO_4$ |
|---|---|---|
| None | None | $H_2O$ |
| None | None | Poly(lys) |
| None | None | Poly(glu) |
| Poly(lys) | None | Poly(lys) |
| Poly(lys) | None | Poly(glu) |
| Poly(glu) | None | Poly(lys) |
| Poly(glu) | None | poly(glu) |
| Poly(lys) | Poly(glu) | Poly(lys) |
| Poly(lys) | Poly(glu) | Poly(glu) |
| Poly(lys) | Poly(glu) | $H_2O$ |

Three foil specimens were mounted on a single stage for each experiment so that identically-prepared samples would be available for further analysis. Foils were immobilized on the stage with wrapped poly(tetrafluoroethylene) films so that a 2.5 mm×5 mm area of each foil was exposed. Foil specimens were exposed to each pre-treatment solution for 12 hours before transfer to the next solution in the sequence or to the desired precipitation medium. All solutions were continually stirred during foil exposure at 200 rpm.

Growth of organoapatites on the pre-treated or freshly-passivated foil was attempted by exposure of the specimens to the modified organoapitite precipitation (FIG. 4). $Ca(OH)_2$ and $H_3PO_4$ reactants were prepared as described previously. The poly(tetrafluroethylene) stage with appropriately prepared foils was immersed in the poly(amino acid) or $H_2O$ precipitation medium prior to transfer of $Ca(OH)_2$ and $H_3PO_4$. The apatite precipitation was then carried out as described in Example 1. The foils were removed from the mother liquor after one hour and rinsed for 1 minute in reagent-grade acetone and three times for 30 seconds each in deionized $H_2O$, followed by drying under vacuum desiccation for 24 hours. Bulk organoapatite by product was recovered from the mother liquor by centrifugation as described previously.

EXAMPLE 3

Hydrolytic Stability Testing

Foils samples from each treatment sequence for which surface growth of organoapatites had been observed were immersed in 10 mL Ringer's solution buffered at a pH 7.4 with Tris-HCl (Sigma) in sealed glass vials. The vials were suspended in a heated water bath maintained at 37° C. After one week, the foils were removed, washed three times in deionized $H_2O$, and dried for 24 hours in a vacuum desiccator. Foils were examined by scanning electron microscopy and analyzed sterologically as to surface coverage and morphology for comparison to identically synthesized controls which were not immersed in Ringer's solution.

EXAMPLE 4

Scanning Electron Microscopy

The foil specimens were mounted on 20 mm tall cylindrical aluminum stubs 10 mm in diameter with colloidal graphite in toluene. Samples were then coated with Au/Pd by sputter deposition in an SPI apparatus (SPI Systems) for 40 seconds at 50 mA under a 170 micron vacuum. Samples were examined in the upper, high-resolution stage of an ISI-130 scanning electron microscope equipped with a $LaB_6$ filament operating at 10 kV. Qualitative energy-dispersive x-ray analysis (EDAX) was performed on an attached system. (Tracor Northern) utilizing a beryllium-filtered detector mounted in the lower (low-resolution) stage. Spectra were collected for 200 seconds at 20 kV. Results are shown in FIG. 10.

EXAMPLE 5

Image Analysis

Ti-6Al-4V foil surfaces were mapped systematically by scanning electron micrography. Sufficient micrographs were produced at 600× magnification to sample at least 10% of the surface exposed to the apatite reaction. Micrographs were digitized utilizing a Silverscan II high-resolution positive schanner operating in 256-level gray-scale mode at 300 dpi and downloading to a Macintosh Quadra system supporting Adobe Photoshop software. Digitized micrographs were analyzed stereologically for surface area utilizing standard techniques. The specified two-phase variation was adapted by considering surface-bounded apatite deposits and clean exposed metal surface as separate phases. Test lines 100 mm long were applied to identically-magnified fields and confidence limits were calculated following the ASTM guidelines. Counts were made separately for each phase to cross-check results. Multiple fields were measured and the date average over the entire sampled surface to ensure an adequate statistical sample size.

EXAMPLE 6

Quantitative Energy-Dispersive X-ray Analysis (EDAX)

Foil specimens were mounted on 15 mm diameter aluminum stubs with colloidal graphite in toluene. Samples were analyzed for Ca and P content with a LINK EDAX system and calibrated against a Cu grid reference. EDAX spectra were collected in point mode for 100 seconds at 20 kV. Organoapitite deposits were also characterized by comparison under secondary and back scattered electron imaging. All images were obtained at 20 kV.

EXAMPLE 7

Discussion on the Growth of Organoapatites on Ti-6Al-4V

Figure 5:
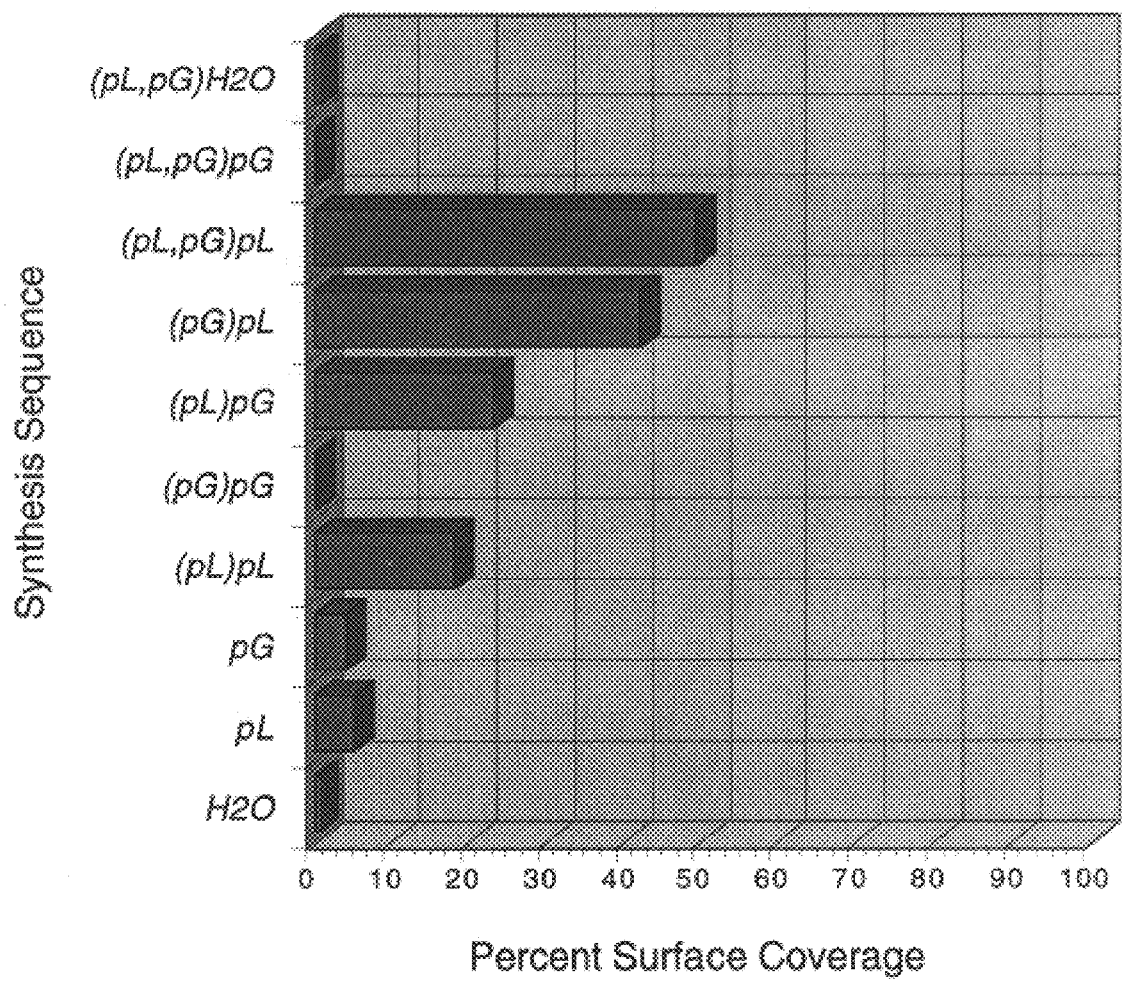
FIG. 5 shows the surface area coverage resulting from organoapatite growth sequences on Ti-6Al-4V foils. Synthesis sequences are coded as follows: pL=poly(lysine), pG=poly (glutamic acid), $H_2O$=distilled $H_2O$. The pretreatment sequences are noted in the parentheses.

The overall scheme for investigating macromolecular-mediated growth of organoapatites on Ti-6Al-4V was described in Example 2. A summary of observed precipitate growth is presented in FIG. 5. The surface coverages were obtained by the stereology procedures detailed in Example 5. No precipitates were observed on foils which had been subjected to a pre-treatment step with poly(glutamic acid) immediately prior to exposure to a poly(glutamic acid) organoapatite reaction step. Isolated deposits no more than 25 um across were observed for foils which had been subjected to a control reaction step where apatites were synthesized in the absence of polymer. These control foils, however, exhibited only a marginal (less than 1%) surface coverage. Likewise, foils which had been exposed only to an organoapatite reaction with poly(lys) or poly(L-sodium glutamate) (poly(glu)) but which were not subjected to any pretreatments (denoted as pLys or pGlu, respectively) displayed highly variable growth of precipitates that was also less than 1% of total area. Foils in which a single pretreatment step with poly(lys) had been followed by an organoapatite reaction with either poly(lys) or poly(glu) (denoted as (pLys)pLys or (pLys)pGlu, respectively, where the pretreatment sequence is indicated in parenthesis) demonstrated moderate surface coverages of 18% and 23%, respectively. A three-step sequence consisting of a pretreatment in poly (lys) followed by pretreatment in poly(glu) and finally exposure to a poly(lys) organoapatite reaction (denoted as (pLys, pGlu)pLys) produced a surface coverage of 49%. A two-step sequence of a poly(glu) pretreatment followed by a poly(lys) reaction (denoted as (pGlu)pLys) showed slightly lower coverage (42%).

Figure 7:
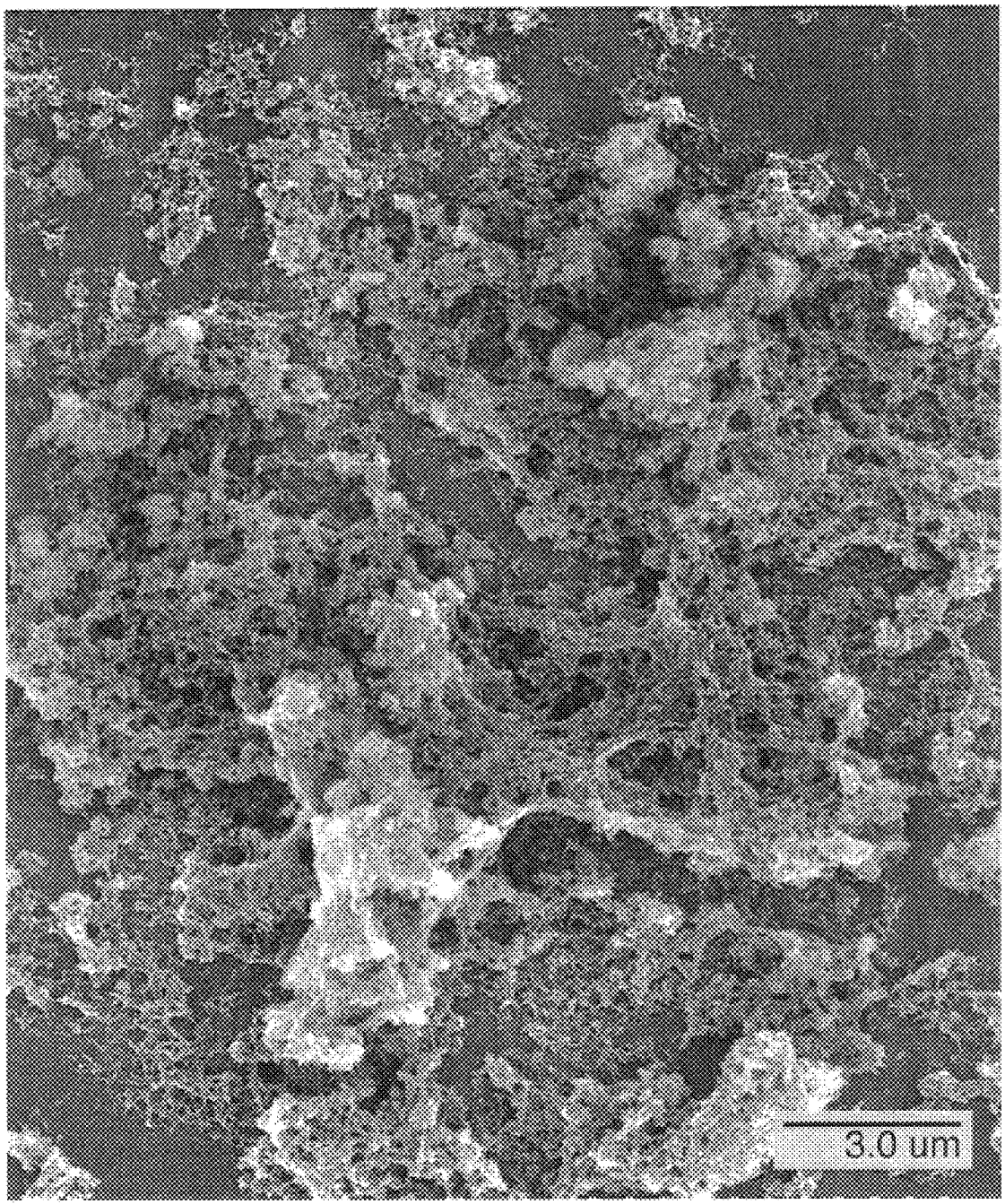
FIG. 7 show SEM of organoapatites grown from poly(L-lysine) (poly(lys)) mother liquor on Ti-6Al-4V surfaces.

At low magnification in the SEM, most organoapatite growth is present in the form of "colonies" of aggregated precipitates whose size and spacing varied depending on the specific synthesis sequence used (See FIG. 6). The poly(lys)/poly(glu) pretreatment followed by a poly(lys) reaction also exhibited small "proto-colonies" of organoapatites on the order of 1 um distributed over the foil surface in between the large colonies. (See FIG. 7). This sequence was the only one which exhibited this kind of dual precipitate architecture.

Figure 9:
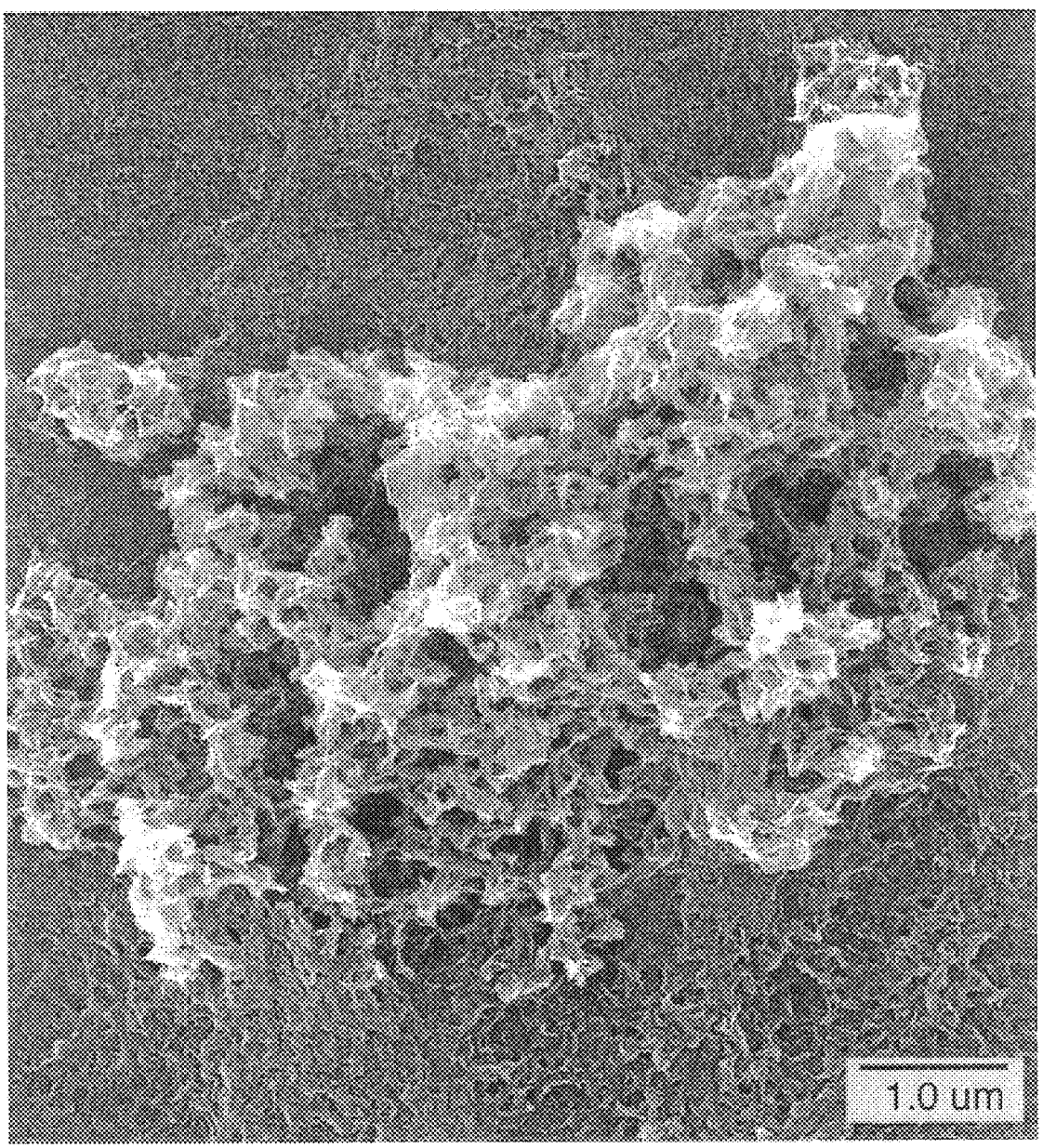
FIG. 9 shows high magnification SEM organoapatites grown on Ti-6Al-4V surfaces from poly(lys) mother liquor.

Morphologies of the surface-bound colonies were remarkably similar at higher magnification. All exhibited the characteristic "coral"-like structure of interconnected fine spicules of material which had previously been observed for bulk organoapatite precipitates. Stupp, S. I.; Ciegler, G. W. *J. Biomed. Mater. Res.* 1992, 26, 169. High magnification scanning electron micrographs (See FIG. 8) of the colonies reveal an abundance of apparently interconnected porosity on the order of 1 to 10 um . The tiny proto-colonies appear as individual spicules of material no larger than 1 um growing from the metal surface (See FIG. 9).

Quantitative energy-dispersive x-ray analysis (EDAX) of the foils revealed that all precipitates observed on the surface generated only Ca and P peaks in addition to the Ti, Al, and V background peaks from the metal itself (See FIG. 10). Scanning electron microscopy of the deposits in back-scattered mode demonstrated significant contrast between the surface precipitates and the clean metal surface (See FIG. 11). The dark patches which were observed at locations of dense precipitates confirm that these deposits are composed of lighter atomic weight elements than the surrounding titanium alloy. These results indicate that the observed surface-bound deposits are indeed composed of calcium phosphates. Quantitative EDAX of the deposits reveal that the calcium phosphate surface precipitates have a Ca/P ratio of approximately 0.9 after 1 hour in the mother liquor.

CONCLUSION AS TO EXAMPLES 2–7

The inventors have found that significant growth of organoapatites on titanium alloys occurs when the alloy surface was pretreated with poly(amino acids). The inventors, while not wishing to be bound by any theory, believe that ionic interactions between oppositely-charged functional groups on the poly(amino acid) may play an important role in determining whether surface deposition is observed.

EXAMPLE 8

Growth of Organoapatites on Surgical Alloy Surface-Metal Plugs

Poly(amino acid) solutions were prepared in 1000 ml three-neck round bottom flasks by the addition of either 0.0666 g poly(L-lysine hydrochloride) (Sigma, St. Louis, Mich.) or 0.0628 g poly(L-sodium glutamate) (Sigma, St. Louis Mo.) to 400 ml deionized water. The pH of each solution was adjusted to 7.4 by the dropwise addition of 6M NaOH or HCl. Each flask was sealed and purged with nitrogen for at least 3 hours.

As received, metal plugs (a gift from Professor Ufrich Gross at the Medical University of the Free University in Berlin, Germany) (8 mm length, 4 mm diameter) with porous surfaces were cut in half and each cut lengthwise to produce four half-cylinder-shaped samples of 4 mm in length and 2 mm radius. Each sample was washed consecutively in deionized water, reagent grade acetone and deionized water while being subjected to ultrasound agitation for 15 minutes. Then they were etched in a solution containing 10:1 ratio of 10 vol. $HNO_3$, 1 vol. % HF, followed by passuration in 40 Vol. % $HNO_3$. Specimens were then rinsed thoroughly in deionized water and dried under vacuum for at least 3 hours. Half cylinder samples were mounted vertically on a custom designed poly(tetrafluroethylene) stage with the porous curved surface exposed and the assembly was immersed in poly(L-lysine hydrochloride) solution. After 12 hours of exposure to this solution, the assembly was taken out and transferred to poly(L-sodium glutamate) solution and left there for 12 hours. Both solutions were continually stirred during immersion of samples at 200 rpm.

Growth of organoapatites on the pretreated plugs was conducted by transferring the samples to the reaction solution containing 400 ml of poly(L-lysine hydrochloride) with the same concentrations as in the pretreatment solution. This solution was prepared in a double-walled glass reactor vessel and the pH was adjusted to 7.4. Water at 37° C. was continuously pumped through the outerjacket of the reactor to maintain a constant temperature. On two separate flasks 500 ml of $Ca(OH)_2$ solution and $H_3PO_4$ solution were prepared with the appropriate iconcentrations to give Ca/P of approximately 1.67. These flasks were immersed in a water bath maintained at 37° C. All solutions were sealed and purged with nitrogen prior to use.

While stirring the poly(L-lysine hydrochloride) solution at 250 rpm, pretreated samples were immersed in the solution and $Ca(OH)_2$ and $H_3PO_4$ solutions (Fisher, Fairfield, N.J.) were transferred to the double-walled reactor vessel through stainless-steel cannulae at equal rates by pressurization with nitrogen gas. During this transfer, pH of the reaction solution in the double-walled vessel was maintained at 7.4 by dropwise addition of NaOH or HCl as necessary. Transfer was accomplished in approximately 5 minutes. After 1 hour, samples were removed from the mother liquor and rinsed for 1 minute in reagent grade acetone and three times for 30 seconds each in deionized water. Samples were then dried under vacuum for 24 hours and characterized by scanning electron microscopy using Hitachi S-800 instrument.

FIG. 1A shows the surface of a surgical alloy plug as viewed by SEM, in FIGS. 1B–1D, show clearly the significant deposition of organoapatite artificial bone on the surface of the alloy.

EXAMPLE 9

Deposition of Organoapatites on an Alloy Cylinder 1 mM solutions of poly(L-lysine hydrochloride) and poly(L-sodium glutamate) were each prepared separately in 500 mL 3-necked round bottom flasks. The 1 mM solution of poly(L-lysine hydrochloride) was prepared by mixing 0.0333 g of poly(L-lysine hydrochloriyde) (Sigma, St. Louis, Mich.) in 200 mL of deionized water. The 1 mM solution of poly(L-sodium glutamate) was prepared by mixing 0.0314 g of poly(L-sodium glutamate) (Sigma, St. Louis, Mich.) in 200 mL of deionized water. The poly(L-lysine hydrogen chloride) and poly(L-sodium glutamate) solutions were then bubbled with $N_2$ (g) for about 5 hours. The pH of each solution was then adjusted to approximately 7.4 using 3M of HCl and/or 3M of NaOH.

A whole, porous metal alloy cylinder (a gift from Professor Ulrich Gross at the Medical University of the Free University, Berlin Germany) was prepared for organoapatite deposition in the following manner. First, the cylinder was cleaned with deionized water and acetone. The cylinder was sonicated in a centrifuge tube containing deionized water for approximately 15 minutes. After 15 minutes, the cylinder was removed from the centrifuge tube and placed in a second centrifuge tube containing acetone. The cylinder was sonicated in the second centrifuge tube for approximately 15 minutes. After 15 minutes, the cylinder was removed from the second centrifuge tube and placed in a third centrifuge tube containing deionized water. The cylinder was then sonicated in the deionized water in the centrflge tube for approximately 15 minutes. The cylinder was then removed from the third centrifuge tube.

The cylinder was then placed in an cleaning solution, 10 vol. % $HNO_3$ and 1 vol. % HF for about five (5) minutes, followed by passivation in 40 Vol.% $HNO_3$ solution. The cylinder was then removed from the cleaning solution and then washed with deionized water. The cylinder was washed six (6) times with deionized water. The cylinder was then sonicated in a centrifuge tube containing deionized water for approximately two minutes. The cylinder was then removed from the centrifuge tube and dried in a desiccated vacuum for at least three hours.

Once the cylinder had sufficiently dried, it was mounted in a holder and submerged in the poly(L-lysine) solution for approximately 20 hours. After 20 hours, the cylinder was removed from the poly(L-lysine) solution and placed in a poly(L-glutamic acid) solution for approximately 20 hours.

500 mL of deionized water was bubbled with $H_3PO_4$ in a 3-necked round bottom flask for at least three hours. Once the deionized water has been sufficiently bubbled with the $N_2$ (g), it was used to prepare a 15 mM $Ca(OH)_2$ solution. The $Ca(OH)_2$ solution was prepared by adding about 0.5557 g of $Ca(OH)_2$(s) (Fisher, Fairfield, N.J.) to the 500mL of $N_2$ (g) bubbled deionized water. The $Ca(OH)_2$ solution was then placed in a refrigerator for three (3) hours.

A 9 mM solution of $H_3PO_4$ was prepared in a 2 liter volumetric flask by adding 1.22 mL of concentrated $H_3PO_4$ (Fisher, Fairfield, N.J.) to an approximate amount of deionized water. 500 ml of the 15 mM $Ca(OH)_2$ solution, 500 mL of 9 mM $H_3PO_4$ solution and 400 mL of deionized water were combined thermostat and bubbled overnight with $N_2$ (g) in a reaction vessel.

A water temperature reservoir was filled with water and the thermostat adjusted to 37° C. A solution of poly(L-lysine hydrochloride) solution was prepared by adding 0.0666 g of poly(L-lysine hydrochloride) (Sigma, St. Louis, Mich.) to 400 mL of $N_2$ (g) bubbled deionized water. The pH was then adjusted to 7.4 using 3M HCl and 3M NaOH. 15 mM of $Ca(OH)_2$ solution and 9 mM $H_3PO_4$ were then added to the water reservoir (37° C.). The water was then pumped into the vessel.

The cylinder was then placed in a vessel. 15 MM $Ca(OH)_2$ solution and 9 mM $H_3PO_4$ was transferred to the vessel using standard $N_2(g)$ pressure. The pH of the solution in the vessel was maintained at 7.4 using 3M HCl and 3M NaOH.

When the transfer was complete and the pH is about 7.4, the vessel was sealed for about one (1) hour. After approximately one (1) hour, the cylinder was removed from the vessel and holder and placed in a centrifuge tube. The cylinder was then washed for 1 minute with acetone. The cylinder was then washed for 30 seconds with deionized water. The washing with the deionized water was repeated three (3) times. The alloy cylinder was then vacuum desiccated for at least twenty-four (24) hours.

Figure 12:
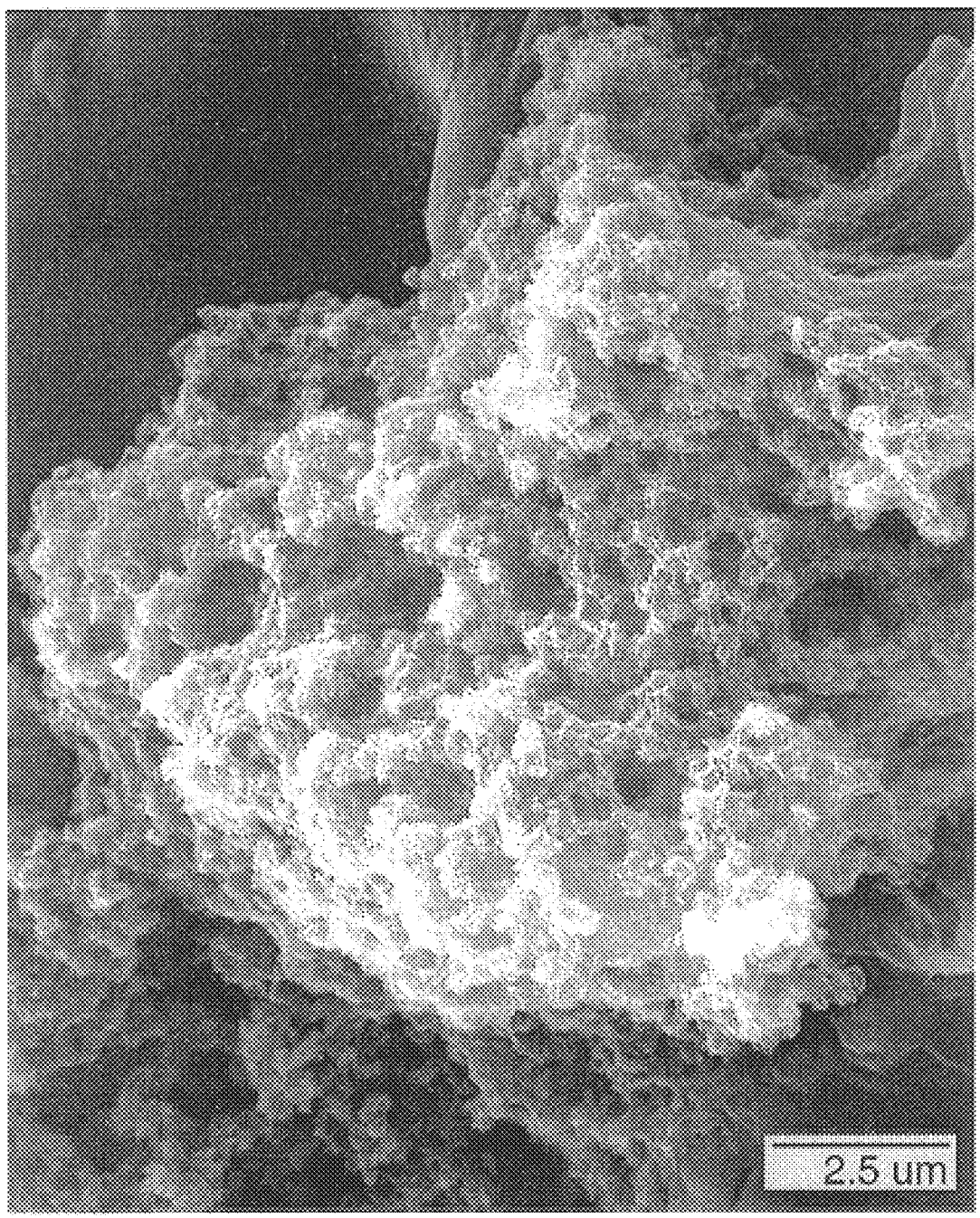
FIG. 12 shows a scanning electron micrograph of organoapatites synthesized on the surface of a porous metal cylinder.

The precipitate in the vessel was then centrifuged at 12,500 rpm, resuspended in acetone and centrifuged, the precipitate was then resuspended in deionized water and then centrifuged for a third time and the precipitate vacuum desiccated for twenty-four (24) hours. After the vacuum desiccation, the material was suitable for use as an artificial bone material. FIG. 12 shows a scanning electron micrography of organoapatites synthesized in the surface of the cylinder using the procedure described in this example. X-ray diffraction and electron diffraction analysis indicated that the organoapatites on the cylinder contained hydroxyapatites.

EXAMPLE 10

Deposition of Organoapatites on an Alloy Foil 1 mM solutions of poly(L-lysine hydrochloride) and poly(L-sodium glutamate) were each prepared separately in 500 mL 3-necked round bottom flasks. The 1 mM solution of poly(L-lysine hydrochloride) was prepared by mixing 0.0333 g of poly(L-lysine hydrochloride) (Sigma, St. Louis, Mo.) in 200 mL of deionized water. The 1 mM solution of poly(L-sodium glutamate) was prepared by mixing 0.0314 g of poly(L-sodium glutamate) (Sigma, St. Louis, Mich.) in 200 mL of deionized water. The poly(L-lysine hydrogen chloride) and poly(L-sodium glutamate) solutions were then bubbled with $N_2$ (g) for about 5 hours. The pH of each solution was then adjusted to approximately 7.4 using 3M HCl and/or 3M of NaOH.

Ti-6Al-4V foil (Good Fellow, Cambridge, UK) was prepared for organoapatite deposition in the following manner. First, the foil was washed with deionized water and acetone. The foil was sonicated in a centrifuge tube containing deionized water for approximately 15 minutes. After 15 minutes, the foil was removed from the centrifuge tube and placed in a second centrifuge tube containing acetone. The foil was sonicated in the second centrifuge tube for approximately 15 minutes. After 15 minutes, the foil was removed from the second centrifuge tube and was placed in an cleaning solution containing 10% $HNO_3$, 17% OH for about five (5) minutes. The foil was then removed from the cleaning solution and then washed with deionized water. The foil was washed six (6) times with deionized water. The foil was then sonicated in a centrifuge tube containing deionized water for approximately two minutes. The foil was then removed from the centrifuge tube and dried in a desiccated vacuum for at least three hours.

Once the foil had sufficiently dried, it was mounted in a holder and submerged in the poly(L-lysine hydrochloride) solution for approximately 20 hours. After 20 hours, the foil was removed from the poly(L-lysine hydrochloride) solution and placed in a poly(L-sodium glutamate) solution for approximately 20 hours.

500 mL of 9 mM $H_3PO_4$ solution was bubbled in a 3-necked round bottom flask for at least three hours. Once the deionized water has been sufficiently bubbled with the $N_2$ (g), it was used to prepare a 15 mM $Ca(OH)_2$ solution. The $Ca(OH)_2$ solution was prepared by adding about 0.5557 g of $Ca(OH)_2(s)$ (Fisher, Fairfield, N.J.) to the 500mL of $N_2$ (g) bubbled deionized water. The $Ca(OH)_2$ solution was then placed in a refrigerator for three (3) hours.

A 2 liter 9 mM $H_3PO_4$ solution was prepared in a volumetric flask by adding 1.22 mL of concentrated $H_3PO_4$ to appropriate amount of deionized water. 500 mL of the 15 mM $Ca(OH)_2(s)$ (Fisher, Fairfield, N.J.) solution, 500 mL of 9 mM $H_3PO_4$ solution and 400 mL of deionized water were placed in and bubbled overnight with $N_2$ (g) in a reaction vessel.

A water temperature reservoir was filled with water and the temperature adjusted to 37° C. A solution of poly(L-lysine hydrochloride) solution was prepared by adding 0.0666 g of poly(L-lysine hydrochloride) to 400 mL of $N_2$ (g) bubbled deionized water. The pH is then adjusted to 7.4 using 3M HCl and 3M NaOH. Flasks with 15 mM of $Ca(OH)_2$ solution and 9 mM $H_3PO_4$ were then immersed in the water reservoir (37° C.). The water is then pumped into the reaction vessel.

The foil is then placed in a vessel. 15 mM $Ca(OH)_2$ solution and 9 mM $H_3PO_4$ is transferred to the vessel using standard $N_2$ (g) pressure. The pH of the solution in the vessel was maintained at 7.4 using 3M HCl and 3M NaOH.

When the transfer is complete and the pH is about 7.4, the vessel is sealed for about one (1) hour. After approximately one (1) hour, the foil was removed from the vessel and holder and placed in a centrifuge tube. The foil was then washed for 1 minute with acetone. The foil then washed for 30 seconds with deionized water. The washing with The deionized water was repeated three (3) times. The alloy foil was then vacuum desiccated for twenty-four (24) hours.

The precipitate in the vessel was then centrifuged, resuspended in acetone and centrifuged, the precipitate was then resuspended in deionized water and then centrifuged for a third time and the precipitate vacuum desiccated for at least twenty-four (24) hours. After the vacuum desiccation, the material was suitable for use as artificial bone material.

Figure 13:
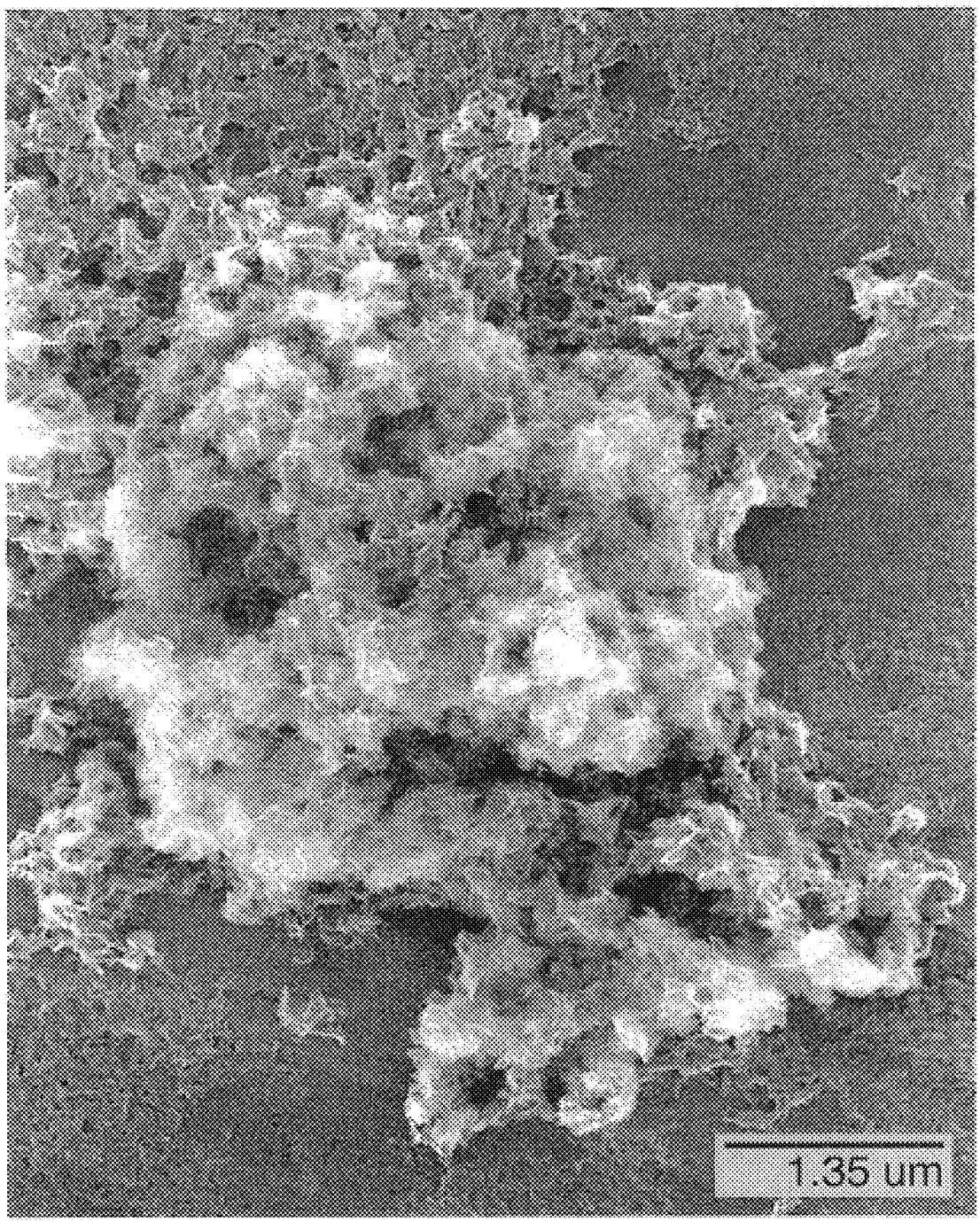
FIG. 13 shows a scanning electron micrograph of organoapatites synthesized on the surface of a metal foil.

FIG. 13 shows a scanning electron micrographs of the synthesis of Iorganoapatites on the Ti-6Al-4V using the procedure described in this example. X-ray diffraction and electron diffraction analysis indicated that the organoapatites on the foil contained hydroxyapatites.

We claim as our invention:

1. A method for synthesizing organoapatites onto the surface of a metal alloy, the method comprising the steps of:

(a) treating the surface of porous metal alloy with an aqueous solution comprising a first poly(amino acid) having a functional group possessing a charge;

(b) treating the surface of the metal alloy with an aqueous solution comprising a second poly(amino acid) having a functional group possessing a charge, wherein the charge of the second poly(amino acid) is opposite to the charge of the functional group of the first poly(amino acid) in step a;

(c) immersing the surface treated metal alloy in an aqueous solution comprising a third poly(amino acid) having a functional group possessing a charge, wherein the charge of the functional group of the third poly(amino acid) is opposite to the charge possessed by the functional group of the second poly(amino acid) used in step b; and (d) synthesizing the organoapatites on the surface of the metal alloy.

2. The method of claim 1 wherein the alloy is cobalt-chromium, stainless steel or titanium.

3. The method of claim 1 wherein the first poly(amino acid) is poly(L-lysine hydrochloride), the second poly(amino acid) is poly(L-sodium glutamate) and the third poly(amino acid) is poly(L-lysine hydrochloride).

4. The method of claim 1 wherein the first poly(amino acid) is poly(L-sodium glutamate), the second poly(amino acid) is poly(l-lysine hydrochloride) and the third poly(amino acid) is poly(L-sodium glutamate).

5. The method of claim 1 further comprising the step of cleaning the metal alloy prior to treating the surface of the alloy with the aqueous solution comprising the first poly(amino acid).

6. The method of claim 1 wherein the metal alloy is treated with the aqueous solution containing the first poly(amino acid) for at least 12 hours.

7. The method of claim 6 wherein the metal alloy is treated with the aqueous solution containing the first poly(amino acid) for at least 20 hours.

8. A method for synthesizing organoapatites onto the surface of a metal alloy, the method comprising the steps of:
(a) treating the surface of a porous metal alloy with an aqueous solution comprising a first poly(amino acid) having a functional group possessing a charge;
(b) treating the surface of the metal alloy with a aqueous solution comprising a poly(electrolyte);
(c) treating the surface treated metal alloy with an aqueous solution comprising a second poly(amino acid) having a functional group possessing a charge, wherein the charge of the second poly(amino acid) is opposite to the charge of the functional group of the first poly(amino acid) used in step (a); and
(d) synthesizing the organoapatites onto the surface of the metal alloy.

9. The method of claim 8 wherein the alloy is cobalt-chromium, stainless steel, titanium or titanium-aluminum-vanadium.

10. The method of claim 8 wherein the first poly(amino acid) is poly(L-lysine hydrochloride), the second poly(amino acid) is poly(L-sodium glutamate) and the third poly(amino acid) is poly(L-lysine hydrochloride).

11. The method of claim 8 wherein the first poly(amino acid) is poly(L-sodium glutamate) and the second poly(amino acid) is poly(l-lysine hydrochloride).

12. The method of claim 8 further comprising the step of cleaning the metal alloy prior to treating the surface of the alloy with the aqueous solution comprising the first poly(amino acid).

13. The method of claim 8 wherein the metal alloy is treated with the aqueous solution containing the first poly(amino acid) for at least 12 hours.

14. The method of claim 13 wherein the metal alloy is treated with the aqueous solution containing the first poly(amino acid) for at least 20 hours.

15. The method of claim 8 wherein the poly(electrolyte) is poly(sodium acrylate).

* * * * *